United States Patent
Butler et al.

(10) Patent No.: US 6,638,350 B2
(45) Date of Patent: Oct. 28, 2003

(54) INK JET INK COMPOSITION

(75) Inventors: Susan Hardin Butler, Lexington, KY (US); Jing X. Sun, Lexington, KY (US)

(73) Assignee: Lexmark International, Inc., Lexington, KY (US)

( * ) Notice: Subject to any disclaimer, the term of this patent is extended or adjusted under 35 U.S.C. 154(b) by 0 days.

(21) Appl. No.: 10/120,867

(22) Filed: Apr. 11, 2002

(65) Prior Publication Data

US 2003/0024434 A1 Feb. 6, 2003

Related U.S. Application Data

(63) Continuation-in-part of application No. 09/916,571, filed on Jul. 27, 2001, now Pat. No. 6,402,825.

(51) Int. Cl.[7] .............................. C09D 11/02; C09C 1/44
(52) U.S. Cl. ................. 106/31.28; 106/31.58; 106/31.86; 106/31.49; 106/31.78; 106/472
(58) Field of Search .................. 106/31.28, 31.58, 106/31.86, 31.49, 31.78, 472

(56) References Cited

U.S. PATENT DOCUMENTS

| | | | | |
|---|---|---|---|---|
| 5,571,311 A | * | 11/1996 | Belmont et al. | 106/31.28 |
| 5,976,233 A | * | 11/1999 | Osumi et al. | 106/31.86 |
| 6,221,141 B1 | * | 4/2001 | Takada et al. | 106/31.6 |
| 6,306,204 B1 | * | 10/2001 | Lin | 106/31.43 |
| 6,332,919 B2 | * | 12/2001 | Osumi et al. | 106/31.6 |
| 6,367,921 B1 | * | 4/2002 | Kurabayashi et al. | 347/101 |
| 6,383,275 B1 | * | 5/2002 | Lin | 106/31.27 |
| 6,402,825 B1 | * | 6/2002 | Sun | 106/473 |
| 6,471,757 B1 | * | 10/2002 | Koitabashi et al. | 106/31.28 |
| 2001/0020431 A1 | * | 9/2001 | Osumi et al. | 106/31.6 |

* cited by examiner

*Primary Examiner*—Mark L. Bell
*Assistant Examiner*—Veronica F. Faison
(74) *Attorney, Agent, or Firm*—Luedeka, Neely & Graham, P.C.

(57) ABSTRACT

The invention provides an ink composition having improved printing performance. The ink composition includes an ink vehicle, from about 0.1 to about 10% by weight self-dispersed ink pigment, from about 0.1 to about 10% by weight dye, a humectant, and a penetrant, wherein the weight ratio of ink pigment to dye ranges from greater than about 0.75:1 to less than about 2.5:1. Such ink compositions exhibit substantially improved permanence, decreased drying time, and high optical density compared to ink compositions containing only ink pigment or dye.

20 Claims, No Drawings

INK JET INK COMPOSITION

RELATED APPLICATION

This application is a continuation-in-part of application Ser. No. 09/916,571, filed Jul. 27, 2001, now U.S. Pat. No. 6,402,825.

FIELD OF THE INVENTION

The invention relates to improved ink compositions containing dyes and pigments and to methods for making improved ink formulations, particularly for ink jet printers.

BACKGROUND OF THE INVENTION

Ink jet recording is an advantageous print method used in many commercial products. Beneficial characteristics include small size, high speed, low cost, and adaptability to various substrates. A common problem with ink jet recording systems involves the formulation of an ink composition that has desirable print characteristics. Ink compositions for ink jet printer applications may be based on dyes or pigment colorants. Dyes are often used in ink compositions because of their stability over time, vibrant color, and excellent dry times. But images printed with dyes are prone to fading and poor water fastness which adversely effect print quality. Ink compositions based on pigment type colorants have improved light fastness and water fastness. However, many pigments are not readily soluble in aqueous solutions and often require the presence of polymeric dispersing agents to improve their dispersibility. Unfortunately, the polymeric dispersing agent tends to increase the viscosity and dry time of the ink and decreases the wettability of the ink with respect to the print media.

As print speed increases for ink jet printers there is a need for improved ink formulations which have acceptable dry times and can produce print with high optical density without decreasing the stability of the ink or idling maintenance time.

SUMMARY OF THE INVENTION

The present invention relates to an ink jet ink composition including an ink vehicle, from about 0.1 to about 10% by weight self-dispersed ink pigment and from about 0.1 to about 10% by weight ink dye. The ink composition also includes a humectant selected from the group consisting of dipropylene glycol, tripropylene glycol, triethylene glycol, tetraethylene glycol, 1,(2,-hydroxyethyl)-2-pyrrolidone, trimethyolpropane, 1,2-propanediol, 1,3-propanediol, 1,5-pentanediol, 2-pyrrolidone, polyethylene glycol, diethylene glycol, 2,2-thiodiethanol, and mixtures thereof; and a penetrant selected from the group consisting of 1,2-hexandiol, hexyl carbitol, diethylene glycol butyl ether, diethylene glycol benzyl ether, n-propyl alcohol, secondary alcohol ethoxylates, ethoxylated acetylenic diols, polyalkyleneoxide modified heptamethyltrisiloxane, and mixtures thereof. The weight ratio of pigment to dye in the ink composition preferably ranges from greater than about 0.75:1 to less than about 2.5:1.

In another aspect the invention provides a method for improving the printing characteristics of an ink jet ink composition. The method includes preparing an ink formulation containing from about 0.1 to about 10% by weight self-dispersed ink pigment, from about 0.1 to about 10% by weight dye, and water. A humectant, a penetrant, and optionally a biocide are mixed with the ink formulation to provide an ink composition. In the composition, the weight ratio of ink pigment to dye ranges from greater than about 0.75:1 to less than about 2.5:1.

An advantage of the invention is that the ink composition exhibits substantially improved permanence and higher optical density than ink compositions containing only dye or only pigment. The ink composition of the invention also dries faster than a conventional ink containing only pigment as the colorant thereby enabling use of the ink on a wider variety of print media than can be used with a conventional ink made only with dye or pigment.

DETAILED DESCRIPTION OF THE PREFERRED EMBODIMENTS

Ink compositions according to the invention include an ink vehicle, preferably water. However, the invention is not limited to use of water as an ink vehicle and thus may be applicable to ink compositions made with organic-based ink vehicles.

An important component of the ink composition is a self-dispersed ink pigment, such as self-dispersed carbon black. Self-dispersed carbon blacks include oxidized carbon blacks, surface modified carbon blacks, and a combination of oxidized and surface modified carbon blacks. Methods for making oxidized carbon black are well known and include reacting carbon black with sodium hypochlorite in an aqueous medium. The proportion by weight of sodium hypochlorite to provide an oxidized carbon black is preferably in a range from about 0.4 to about 5.25 parts hypochlorite per part carbon black by weight. U.S. Pat. No. 3,347,632 to Parker describes a preferred method for making oxidized carbon black and the disclosure is incorporated by reference as if fully set forth herein. A particularly preferred carbon black for making oxidized carbon black is a neutral carbon black available from Cabot Corporation of Billerica, Mass. under the trade name MONARCH 880.

Other self-dispersed pigment concentrates useful for the ink formulations of the invention are available from Cabot Corporation of Boston Mass. under the trade names CAB-O-JET 250 (cyan), CAB-O-JET 260 (magenta), CAB-O-JET 270 (yellow), CAB-O-JET 200 (black), and CAB-O-JET 300 (black), and from Orient Chemicals Industries, Ltd. Of Osaka, Japan under the trade names BONJET BLACK CW-1 and BONJET BLACK CW-2. The foregoing pigments are believed to have surface modification which enables the pigments to readily disperse in an aqueous medium without a dispersant.

The self-dispersed ink pigments may be further improved to increase the idle time of the ink formulation by further modifying the surface of the ink pigment. In the case of oxidized carbon black as the self-dispersed pigment, the surface of the oxidized carbon black is preferably further modified by adding steric inducing groups to the surface of the carbon black. Carbon black pigment oxidized with sodium hypochlorite contains carboxyl, hydroxyl, and/or carbonyl groups on its surface. The carboxyl groups on the surface of the carbon black provide sites for reaction with steric inducing compounds. Oxidized carbon black for reaction with such steric inducing compounds preferably has an acid number ranging from about 0.01 to about 1.5 milliequivalents COOH/gram of carbon black, more preferably from about 0.1 to about 0.7 millequivalents COOH/gram of carbon black.

In one step of the reaction, oxidized carbon black is reacted with an amount of thionyl halide to provide organic acid halide groups on the surface of the carbon black. The halide groups of the thionyl halide may be a chloride, bromide, iodide, or fluoride group. Of the thionyl halides, thionyl chloride is a preferred thionyl halide which provides organic acid chloride groups on the surface of the carbon black. The amount of thionyl halide reacted with the carbon black preferably ranges from about 1 to about 20 mole equivalents per COOH group on the carbon black with approximately 10 mole equivalents per COOH group on the carbon black being most preferred. It is preferred to react all of the acid groups on the carbon black with thionyl halide, hence the use of excess thionyl halide is preferred which may also act as a solvent for the reaction.

The reaction between the oxidized carbon black and the thionyl halide is preferably carried out in the presence of a solvent. The preferred solvent is an inert organic solvent. The particularly preferred solvents include, but are not limited to, methylene chloride, tetrahydrofuran, xylene, chloroform, 1,4-dioxane, toluene and other aprotic solvents.

While the order of reactant addition is not limited, the preferred order includes the addition of the thionyl halide to the solvent. Subsequently, this solution is added to a reaction vessel containing the oxidized carbon black.

The reaction is preferably conducted under an atmosphere of inert gas. A particularly preferred inert gas atmosphere for conducting the reaction is a nitrogen gas atmosphere. During the reaction, the temperature of the reaction mass is preferably controlled at a range from about 30° C. to about 55° C. Depending upon the solvent used, reflux may occur. Reaction times may range from about 4 to about 8 hours during which the reaction mass is stirred.

After reacting the oxidized carbon black with thionyl halide, the resulting carbon black having acid halide groups on the surface is isolated from the reaction mixture. Preferably, the reaction product is cooled to about 0° C. to about 5° C. After cooling, the product is filtered under a vacuum and is then washed with a dry solvent. In an alternate purification method, the reaction product is vacuum distilled to yield carbon black having acid halide groups on the surface thereof to provide an acid halide modified carbon black.

The acid halide modified carbon black is then reacted with a predetermined amount of a steric inducing compound. The amount of the steric inducing compound reacted with the carbon black preferably ranges from about 0.2 to about 0.9 milliequivalents per milliequivalent of acid halide modified carbon black. A preferred class of steric inducing compounds include monoalkoxy-terminated polyalkylene glycol compounds comprising an alkylene group containing from 2 to 6 carbon atoms and an alkyl group containing from 1 to 6 carbon atoms. Representative monoalkoxy-terminated polyalkylene glycol compounds include, but are not limited to triethylene glycol monomethyl ether, diethylene glycol monomethyl ether, triethyleneglycol monoethyl ether, diethylene glycol monoethyl ether, triethylene glycol monopropyl ether, diethylene glycol monopropyl ether, triethylene glycol monobutyl ether, diethylene glycol monobutyl ether and the like and mixtures thereof.

Other mono-terminated glycol reactants may be reacted with the acid halide modified carbon black to lower the acid number of the carbon black without adversely affecting the water dispersibility thereof. Such glycol reactants have weight average molecular weights ranging from about 100 to about 1000 and include, but are not limited to, methoxypolyethylene glycol, poly(ethylene glycol) tetrahydrofurfuryl ether, polyoxyethylene or polypropylene oxide nonyl phenyl ether and substituted derivatives of phenyl ether and nonyl phenyl ether.

Mono-amine terminated compounds may also be used as the steric inducing compound provided they are soluble in the organic components of the ink composition and reactive with an organic acid halide. Such compounds include, but are not limited to, alkoxy-terminated Jeffamine polyalkylene glycols having a weight average molecular weight ranging from about 500 to about 2500, methoxy-terminated Jeffamine polyethylene glycol, methoxy-terminated Jeffamine polypropylene glycol and methoxy-terminated Jeffamine polyethylene glycol/polypropylene glycol copolymer. The Jeffamine compounds contain primary amino groups attached to the terminus of a polyether backbone also referred to as "polyether amines." The polyether backbone is based either on propylene oxide (PO), ethylene oxide (EO), or mixed EO/PO. Such amine-terminated compounds may be primary amines or secondary amines.

Other compounds reactive with the organic acid halide groups on the carbon black and soluble in the organic components of the ink composition include, but are not limited to, mono-hydroxy containing compounds such as 2-hydroxyethylpyrrolidone, 2-hydroxyethylmorpholine and 2-hydroxyethyl-oxazolidone and the like.

The reaction between the acid halide groups on the carbon black and the steric inducing compound is preferably carried out in the presence of an amount of inert solvent. The preferred solvent is an organic solvent. Particularly preferred solvents include, but are not limited to, methylene chloride, tetrahydrofuran, xylene, chloroform, 1,4-dioxane, toluene and other aprotic solvents.

The reaction mass also preferably includes a weak base which inhibits reaction by-products of hydrohalic acids. The preferred base is an amine and, most preferably, a tertiary amine. A particularly preferred tertiary amine is triethylamine. The preferred amount of tertiary amine in the reaction mass preferably ranges equivalent to the milliequivalents of organic acid halide in the reaction mass. Another useful amine for inhibiting by-product reactions includes pyridine.

While the order of reactant addition is not limited, the preferred order consists of the addition of the organic solvent to the reaction vessel containing the acid halide modified carbon black. Subsequently, the tertiary amine and the steric inducing compound are added dropwise to the reaction mass in solution with an organic solvent.

During the addition of reactants, the reaction mixture is preferably maintained at a temperature ranging from about 0° C. to about 5° C. The mixture is also preferably stirred for about 10 to about 24 hours during which time the reaction is allowed to warm to room temperature, which is preferably between about 18° C. to about 24° C. When the reaction is substantially complete, the resulting mixture is treated to remove the solvent. The preferred treatment is vacuum distillation. An alternate treatment includes drying the mixture in an oven. An oven temperature of about 60° C. to about 80° C. is preferred with a dry time of about 30 to about 90 minutes.

Once purified, the mixture is washed with water and redispersed in a basic aqueous solution. The basic solution preferably consists of a metal or ammonium hydroxide with the metal being selected from the group consisting of alkali metals, alkaline earth metals, and transition metals. A particularly preferred basic solution is a 20% solution of potassium hydroxide. A sufficient amount of basic solution is added to the product to achieve a predetermined pH in the range from about 7.0 to about 8.5. The basic solution and carbon black product are preferably mixed for about 10 to about 60 minutes to remove any remaining free acid and/or halide ions from the product and to obtain the predetermined pH.

The surface modified carbon black made according to the foregoing procedure has an acid number preferably ranging from about 0.01 to about 1.5, most preferably from about 0.1 to about 0.7 milliequivalents COOH/gram of carbon black. It is further preferred that the surface modified carbon black have an average particle size ranging from about 100 to about 200 nanometers.

The self-dispered ink pigment is preferably present in the ink composition in an amount ranging from about 1 to about 10% by weight of the total ink composition. A particularly preferred amount of self-dispersed ink pigment ranges from about 1 to about 2.5% by weight of the total ink composition.

A second important component of the ink composition is a dye. Dyes which are commonly used in ink jet ink formulations include acid dyes, direct dyes, food dyes, and reactive dyes which may be cyan, magenta, yellow or black. Any dyes which permit the formation of colored visible images on a recording medium may be used. An illustrustive list of such dyes includes, but is not limited to, nitro dyes, nitroso dyes, azo dyes such as mono-azo, di-azo and poly-azo dyes, mordant dyes, preformed metal complexes such as formazan copper complexes, pyrazolones and stilbenes, thiazoles, diphenylmethanes, triphenylmethanes, xanthenes, cridines, azines, oxazines, thiazines, quinines and indigoids. It is particularly preferred that the dye be water soluble.

Illustrative black dyes include, but are not limited to, direct dyes such as C.I. Direct Black 2, 4, 9, 11, 14, 17, 19, 22, 27, 32, 36, 41, 48, 51, 56, 62, 71, 74, 75, 77, 78, 80, 105, 106, 107, 108, 112, 113, 117, 132, 146, 154, 168, 171, and 194. Particularly preferred Direct Black dyes for use in the ink compositions of the invention include Direct Black 154 and Direct Black 168. Acid dyes such as C.I. Acid Black 1, 2, 7, 16, 17, 24, 26, 28, 31, 41, 48, 52, 58, 60, 63, 94, 107, 109, 112, 118, 119, 121, 122, 131, 155, and 156 may also be used. Additionally, the black dye may be selected from basic dyes such as C.I. Basic Black 2 and 8, reactive dyes such as C.I. Reactive Black 1, 3, 5, 6, 8, 12, and 14, and food dyes such as C.I. Food Black 1 and 2. Accordingly, other preferred black dyes include ILFORD K-1334, ILFORD K-1332 available from Ilford Imaging USA, Inc. of Paramus, N.J., Fast Black, Basacid Black X38 and Bayscript Special Black SP. The amount of dye in the ink composition also preferably ranges from about 1 to about 10% by weight of the total ink composition. A particularly preferred amount of dye ranges from about 1 to about 2.5% by weight of the total ink composition.

Unlike other ink compositions, the ink jet ink composition of the invention has a weight ratio of ink pigment to dye which ranges from about 0.5:1 to less than about 3.0:1, preferably from about 0.75:1 to about 2.5:1. Such ratios of ink pigment to dye are effective to provide the advantages of the invention, namely improved permanence and optical density without adversely affecting drying times and/or idling maintenance.

Other ingredients in the ink composition according to the invention include a humectant and a penetrant. Humectants may be selected from the group consisting of dipropylene glycol, tripropylene glycol, triethylene glycol, tetraethylene glycol, 1,(2,-hydroxyethyl)-2-pyrrolidone, trimethyolpropane, 1,2-propanediol, 1,3-propanediol, 1,5-pentanediol, 2-pyrrolidone, polyethylene glycol, diethylene glycol, 2,2-thiodiethanol, and mixtures thereof. A particularly preferred humectant is a mixture of polyethylene glycol having a number average molecular weight of about 400 (PEG 400) and 2-pyrrolidone. The amount of PEG 400 in the ink composition preferably ranges from about 3 to about 10 percent by weight, most preferably from about 7 to about 8 percent by weight based on the total weight of the ink composition. The amount of 2-pyrrolidone in the ink composition also preferably ranges from about 3 to about 10 percent by weight, most preferably from about 7 to about 8 percent by weight based on the total weight of the ink composition.

Penetrants may be selected from the group consisting of 1,2-hexandiol, hexyl carbitol, diethylene glycol butyl ether, diethylene glycol benzyl ether, n-propyl alcohol, secondary alcohol ethoxylates such as TERGITOL 15-S-7 and TERGITOL 15-S-9 available from Union Carbide of Danbury, Conn., ethoxylated acetylenic diols such as SURFYNOL 465 and SURFYNOL 485 available from Air Products and Chemicals, Inc. of Allentown, Pa., polyalkyleneoxide modified heptamethyltrisiloxane such as the SILWET L series available from Loveland Industries, Inc. of Greeley, Colo., and mixtures thereof. A particularly preferred penetrant is a mixture of diethylene glycol monohexyl ether (n-hexyl carbitol) and 1,2-hexanediol. A preferred amount of hexyl carbitol in the ink composition ranges from about 0.1 to about 1.0 percent by weight, most preferably from about 0.3 to about 0.5 percent by weight based on the total weight of the ink composition. The amount of hexanediol in the ink composition preferably ranges from about 0.5 to about 5 percent by weight, most preferably from about 1 to about 3 percent by weight based on the total weight of the ink composition.

Other conventional additives may also be included in the ink composition such as biocides, mildew proofing agents, pH adjustors, antioxidants, conductivity modifiers, and oxygen-absorbing agents. Specific examples of biocides include sodium benzoate, sodium pentacholorphenol, sodium 2-pyridinethiol-1-oxide, sodium dehydroactate and 1,2-benzisothiazolin-3-one (PROXEL GXL).

The order of addition of the components to provide the ink composition is not particularly critical to the invention. However, a preferred order for making the formulation is to add the dye and self-dispersed pigment as a pigment concentrate to water, then add the other components, i.e., the humectants, the penetrants and the biocide to the dye and pigment mixture. The components are thoroughly mixed to provide the ink composition.

EXAMPLE 1

In order to demonstrate the effectiveness of ink compositions according to the invention for improving the printing performance of ink jet inks, the following ink composition was made with black self-dispersed pigment and black dye:

TABLE 1

| Ingredient | Weight % in Composition |
| --- | --- |
| Black Dye (ILFORD K-1334) | 2 |
| Lexmark self-dispersed Black Pigment[1] | 2 |
| PEG 400 | 7.5 |
| 2-pyrrolidone | 7.5 |
| 1,2-hexanediol | 2 |
| n-hexyl carbitol | 0.4 |

TABLE 1-continued

| Ingredient | Weight % in Composition |
|---|---|
| PROXEL GXL | 0.2 |
| Water | Balance |

[1]Lexmark self-dispersed Black Pigment is a sterically modified, oxidized carbon black available from Lexmark International, Inc. of Lexington Kentucky.

EXAMPLE 2

Printing was performed with the ink composition of Example 1 and a with Lexmark Black Pigment Ink 12A1970 on a variety of paper substrates to determine the drying time of the inks. The text file used to determine dry time was printed with a Lexmark Z51 printer. Immediately after printing the printed sheet and a blank sheet of Boise Cascade X9000 paper were fed through a nip with about 0.5 pounds of force. The dry time was determined as the amount of time for substantially zero transfer from the printed sheet to the blank sheet. The following table contains the results:

TABLE 2

| Ink Composition | Fox River Bond | Boise Cascade X9000 | Hammermill Laser Print | Average |
|---|---|---|---|---|
| Ink of Ex. 1 | 9 sec. | 3 sec. | 0.51 sec. | 4.17 sec. |
| 12A1970 | 15 sec. | 10 sec. | 9 sec. | 11.33 sec. |

As shown by the foregoing comparison, the ink composition according to the invention dried 1.5 to 17.5 times faster than a conventional black pigment ink depending on the paper substrate used. On the average, the ink composition of the invention is expected to dry almost three times faster than a conventional black pigment ink. Accordingly, higher speed printing using the ink composition of the invention may be achieved.

EXAMPLE 3

Another advantage of the ink composition of the invention is the improvement in optical density over a dye based ink or a pigment based ink. The optical density was measured on a 0.75 inch by 0.75 inch black block printed with each of the ink compositions. The ink composition of Example 1 and the 12A1970 ink (Lexmark self-dispersed Black Pigment Ink) were printed with a Lexmark Z51 printer. The 12A1030 (Lexmark Black Dye Ink) was printed with a Lexmark 2050 printer. The following table shows the resulting optical densities for each of the inks tested on a variety of paper substrates.

TABLE 3

| Ink Composition | Fox River Bond | Boise Cascade X9000 | Hammermill Laser Print | Average |
|---|---|---|---|---|
| Ink of Ex. 1 | 1.45 | 1.5 | 1.41 | 1.45 |
| 12A1970 | 1.43 | 1.36 | 1.17 | 1.32 |
| 12A1030 | 1.4 | 1.48 | 1.29 | 1.39 |

As demonstrated by the foregoing comparison, the ink composition of the invention had an optical density ranging from about 1.41 to about 1.5 whereas the pigment based ink optical density ranged from 1.17 to 1.43 and the dye based ink composition optical density ranged from 1.29 to 1.48 depending on the paper substrate. In all of the tests, the ink composition of the invention had consistently higher optical density for each of the types of paper substrates used and an overall higher optical density than a convention dye based ink or pigment based ink.

It is contemplated, and will be apparent to those skilled in the art from the foregoing specification that modifications and/or changes may be made in the embodiments of the invention. Accordingly it is expressly intended that the foregoing are only illustrative of the preferred embodiments and are not limiting thereto and that the true spirit and scope of the present invention be determined by reference to the appended claims.

What is claimed is:

1. An ink jet ink composition comprising an ink vehicle, from about 0.1 to about 10% by weight self-dispersed ink pigment; from about 0.1 to about 10% by weight dye; a humectant selected from the group consisting of dipropylene glycol, tripropylene glycol, triethylene glycol, tetraethylene glycol, 1,(2,-hydroxyethyl)-2-pyrrolidone, trimethyolpropane, 1,2-propanediol, 1,3-propanediol, 1,5-pentanediol, 2-pyrrolidone, polyethylene glycol, diethylene glycol, 2,2-thiodiethanol, and mixtures thereof; and a penetrant selected from the group consisting of 1,2-hexandiol, hexyl carbitol, diethylene glycol butyl ether, diethylene glycol benzyl ether, n-propyl alcohol, secondary alcohol ethoxylates, ethoxylated acetylenic diols, polyalkyleneoxide-modified heptamethyl-trisiloxane, and mixtures thereof, wherein the weight ratio of ink pigment to dye ranges from greater than about 0.75:1 to less than about 2.5:1, and wherein the self-dispersed ink pigment comprises an oxidized carbon black having a surface containing a steric inducing group thereon obtained by reacting the carbon black with thionyl halide and a steric inducing compound selected from the group consisting of a monoalkoxy-terminated polyalkylene glycol, a mono-amine terminated polyalkylene glycol compound, 2-hydroxyethylpyrrolidinone, 2-hydroethylmorpholine, and 2-hydroxyethyloxazolidone.

2. The ink jet ink composition of claim 1, wherein the oxidized carbon black has an acid number ranging from about 0.1 to about 0.7 milliequivalents COOH/gram of carbon black.

3. The ink jet ink composition of claim 1, wherein the humectant comprises a mixture of polyethylene glycol and 2-pyrrolidone.

4. The ink jet ink composition of claim 1, wherein the penetrant comprises a mixture of 1,2-hexandiol and hexyl carbitol.

5. The ink jet ink composition of claim 1, containing from about 1 to about 2.5 wt. % self-dispersed ink pigment, from about 1 to about 2.5 wt. % dye, from about 6 to about 8.5 wt. % polyethylene glycol, from about 6 to about 8.5 wt. % 2-pyrrolidone, from about 1 to about 3 wt. % 1,2-hexandiol, and from about 0.1 to about 1 wt. % hexyl carbitol.

6. The ink jet ink composition of claim 1, wherein the ink vehicle comprises water.

7. The ink jet ink composition of claim 1, comprising from about 0.1 to about 1 wt. % hexyl carbitol.

8. A method for improving the printing characteristics of an ink jet ink composition comprising preparing an ink formulation containing from about 0.1 to about 10% by weight self-dispersed ink pigment, from about 0.1 to about 10% by weight dye, and water and mixing a humectant, a penetrant, and optionally a biocide with the ink formulation to provide an ink composition, wherein the weight ratio of ink pigment to dye in the ink composition ranges from greater than about 0.75:1 to less than about 2.5:1, and wherein the self-dispersed ink pigment comprises self-dispersed carbon black having a surface modified by reacting the self-dispersed carbon black with thionyl halide and then with a steric inducing compound selected from the group consisting of a monoalkoxy-terminated polyalkylene glycol compound, a mono-amine terminated compound, 2-hydroxyethylpyrrolidinone, 2-hydroethylmorpholine, and 2-hydroxyethyloxazolidone to provide a steric inducing group on the carbon black.

9. The method of claim 8, wherein the humectant comprises a compound selected from the group consisting of dipropylene glycol, tripropylene glycol, triethylene glycol, tetraethylene glycol, 1,(2,-hydroxyethyl)-2-pyrrolidone, trimethyolpropane, 1,2-propanediol, 1,3-propanediol, 1,5-pentanediol, 2-pyrrolidone, polyethylene glycol, diethylene glycol, 2,2-thiodiethanol, and mixtures thereof.

10. The method of claim 8, wherein the penetrant comprises a compound selected from the group consisting of 1,2-hexandiol, hexyl carbitol, diethylene glycol butyl ether, diethylene glycol benzyl ether, n-propyl alcohol, secondary alcohol ethoxylates, ethoxylated acetylenic diols, polyalkyleneoxide modified heptamethyltrisiloxane, and mixtures thereof.

11. The method of claim 8, wherein self-dispersed carbon black, has an acid number of about 0.5 to about 1.5 milliequivalents COOH/gram of carbon black.

12. The method of claim 8, wherein the humectant comprises a mixture of polyethylene glycol and 2-pyrrolidone.

13. The method of claim 8, wherein the penetrant comprises a mixture of 1,2-hexandiol and hexyl carbitol.

14. An ink jet printer containing an ink jet ink composition comprising an ink vehicle, from about 0.1 to about 10% by weight self-dispersed ink pigment; from about 0.1 to about 10% by weight dye; a humectant selected from the group consisting of dipropylene glycol, tripropylene glycol, triethylene glycol, tetraethylene glycol, 1,(2,-hydroxyethyl)-2-pyrrolidone, trimethyolpropane, 1,2-propanediol, 1,3-propanediol, 1,5-pentanediol, 2-pyrrolidone, polyethylene glycol, diethylene glycol, 2,2-thiodiethanol, and mixtures thereof; and a penetrant selected from the group consisting of 1,2-hexandiol, hexyl carbitol, diethylene glycol butyl ether, diethylene glycol benzyl ether, n-propyl alcohol, secondary alcohol ethoxylates, ethoxylated acetylenic diols, polyalkyleneoxide-modified heptamethyl-trisiloxane, and mixtures thereof, wherein the weight ratio of ink pigment to dye ranges from greater than about 0.75:1 to less than about 2.5:1, and wherein the self-dispersed ink pigment comprises an oxidized carbon black having a surface containing a steric inducing group thereon obtained by reacting the carbon black with thionyl halide and a steric inducing compound selected from the group consisting of a monoalkoxy-terminated polyalkylene glycol, a mono-amine terminated polyalkylene glycol compound, 2-hydroxyethylpyrrolidinone, 2-hydroethylmorpholine, and 2-hydroxyethyloxazolidone.

15. The ink jet printer of claim 14, wherein the oxidized carbon black has an acid number ranging from about 0.1 to about 0.7 milliequivalents COOH/gram of carbon black.

16. The ink jet printer of claim 14, wherein the humectant comprises a mixture of polyethylene glycol and 2-pyrrolidone.

17. The ink jet printer of claim 14, wherein the penetrant comprises a mixture of 1,2-hexandiol and hexyl carbitol.

18. The ink jet printer of claim 14, wherein the ink composition contains from about 1 to about 2.5 wt. % self-dispersed ink pigment, from about 1 to about 2.5 wt. % dye, from about 6 to about 8.5 wt. % polyethylene glycol, from about 6 to about 8.5 wt. % 2-pyrrolidone, from about 1 to about 3 wt. % 1,2-hexandiol, and from about 0.1 to about 1 wt. % hexyl carbitol.

19. The ink jet printer of claim 14, wherein the ink vehicle comprises water.

20. The ink jet printer of claim 14, wherein the ink composition comprises from about 0.1 to about 1 wt. % hexyl carbitol.

* * * * *